(12) United States Patent
Thompson (10) Patent No.: US 7,515,956 B2
(45) Date of Patent: Apr. 7, 2009

(54) TEMPLATE BASED AV/VA INTERVAL COMPARISON FOR THE DISCRIMINATION OF CARDIAC ARRHYTHMIAS

(75) Inventor: Julie Thompson, Circle Pines, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 374 days.

(21) Appl. No.: 10/844,475

(22) Filed: May 12, 2004

(65) Prior Publication Data

US 2005/0256544 A1   Nov. 17, 2005

(51) Int. Cl.
  *A61B 5/0452*  (2006.01)
  *A61B 5/0464*  (2006.01)
  *A61B 5/0468*  (2006.01)

(52) U.S. Cl. ..................... 600/518; 600/516
(58) Field of Classification Search .................. 607/14, 607/25; 600/515, 516, 518
See application file for complete search history.

(56) References Cited

U.S. PATENT DOCUMENTS

| | | | |
|---|---|---|---|
| 4,336,810 A | 6/1982 | Anderson et al. | 128/702 |
| 4,515,161 A | 5/1985 | Wittkampf et al. | 128/419 |
| 4,531,527 A | 7/1985 | Reinhold, Jr. et al. | 128/696 |
| 4,543,963 A | 10/1985 | Gessman | 128/702 |
| 4,572,192 A | 2/1986 | Jackman et al. | 128/419 PG |
| 4,577,634 A | 3/1986 | Gessman | 128/419 PG |
| 4,583,553 A | 4/1986 | Shah et al. | 128/704 |
| 4,721,114 A | 1/1988 | DuFault et al. | 128/696 |
| 4,802,483 A | 2/1989 | Lindgren | 128/419 PG |
| 4,802,491 A | 2/1989 | Cohen et al. | 600/509 |
| 4,832,038 A | 5/1989 | Arai et al. | |
| 4,838,278 A | 6/1989 | Wang et al. | 128/697 |
| 4,860,749 A | 8/1989 | Lehmann | 128/419 PG |

(Continued)

FOREIGN PATENT DOCUMENTS

EP   0469817 A2   2/1992

(Continued)

OTHER PUBLICATIONS

Duru, Firat, et al., "The Potential for Inappropriate Ventricular Tachycardia Confirmation Using the Intracardiac Electrogram (EGM) Width Criterion", *PACE*, vol. 22, 1999, (Jul. 1999),1039-1046.

(Continued)

*Primary Examiner*—Carl H. Layno
*Assistant Examiner*—Tammie K. Heller
(74) *Attorney, Agent, or Firm*—Schwegman, Lundberg & Woessner, P.A.

(57) ABSTRACT

An implantable cardioverter/defibrillator includes a tachycardia detection system that detects one-to-one (1:1) tachycardia, which is a tachycardia with a one-to-one relationship between atrial and ventricular contractions. When the 1:1 tachycardia is detected, the system discriminates ventricular tachycardia (VT) from supraventricular tachycardia (SVT) based on analysis of a cardiac time interval. Examples of the cardiac time interval include an atrioventricular interval (AVI) and a ventriculoatrial interval (VAI). A template time interval is created during a known normal sinus rhythm. The system measures a tachycardia time interval after detecting the 1:1 tachycardia, and indicates a VT detection if the tachycardia time interval differs from the template time interval by at least a predetermined percentage of the template time interval.

42 Claims, 5 Drawing Sheets

U.S. PATENT DOCUMENTS

| | | | |
|---|---|---|---|
| 4,869,252 A | 9/1989 | Gilli | 128/419 PG |
| 4,884,345 A | 12/1989 | Long | 33/1 C |
| 4,924,875 A | 5/1990 | Chamoun | 600/509 |
| 4,947,857 A | 8/1990 | Albert et al. | 128/696 |
| 5,000,189 A | 3/1991 | Throne et al. | 128/702 |
| 5,014,284 A | 5/1991 | Langer et al. | 375/30 |
| 5,014,698 A | 5/1991 | Cohen | 128/419 |
| 5,020,540 A | 6/1991 | Chamoun | 128/696 |
| 5,107,850 A | 4/1992 | Olive | 128/705 |
| 5,139,028 A | 8/1992 | Steinhaus et al. | 128/697 |
| 5,156,148 A | 10/1992 | Cohen | 128/419 PG |
| 5,184,615 A | 2/1993 | Nappholz et al. | 128/419 PG |
| 5,193,550 A | 3/1993 | Duffin | 129/697 |
| 5,205,283 A | 4/1993 | Olson | |
| 5,215,098 A | 6/1993 | Steinhaus et al. | 128/702 |
| 5,217,021 A | 6/1993 | Steinhaus et al. | 128/702 |
| 5,228,438 A | 7/1993 | Buchanan | 128/419 PG |
| 5,240,009 A | 8/1993 | Williams | 128/702 |
| 5,243,980 A | 9/1993 | Mehra | 607/6 |
| 5,247,021 A | 9/1993 | Fujisawa et al. | 525/254 |
| 5,253,644 A | 10/1993 | Elmvist | 607/14 |
| 5,255,186 A | 10/1993 | Steinhaus et al. | 364/413 |
| 5,271,411 A | 12/1993 | Ripley et al. | 128/702 |
| 5,273,049 A | 12/1993 | Steinhaus et al. | 128/696 |
| 5,275,621 A | 1/1994 | Mehra | 607/5 |
| 5,280,792 A | 1/1994 | Leong et al. | 128/702 |
| 5,282,836 A | 2/1994 | Kreyenhagen et al. | 607/4 |
| 5,291,400 A | 3/1994 | Gilham | |
| 5,292,348 A | 3/1994 | Saumarez et al. | 607/5 |
| 5,311,874 A | 5/1994 | Baumann et al. | 128/705 |
| 5,312,445 A | 5/1994 | Nappholz et al. | 607/9 |
| 5,313,953 A | 5/1994 | Yomtov et al. | 128/696 |
| 5,327,900 A | 7/1994 | Mason et al. | 128/705 |
| 5,342,402 A | 8/1994 | Olson et al. | 607/5 |
| 5,351,696 A | 10/1994 | Riff et al. | 128/702 |
| 5,360,436 A | 11/1994 | Alt et al. | 607/18 |
| 5,366,487 A | 11/1994 | Adams et al. | 607/5 |
| 5,370,125 A | 12/1994 | Mason et al. | 128/705 |
| 5,379,776 A | 1/1995 | Murphy et al. | |
| 5,388,578 A | 2/1995 | Yomtov et al. | 128/642 |
| 5,400,795 A | 3/1995 | Murphy et al. | 128/702 |
| 5,403,352 A | 4/1995 | Rossing | |
| 5,411,031 A | 5/1995 | Yomtov | 128/706 |
| 5,431,693 A | 7/1995 | Schroeppel | |
| 5,447,519 A | 9/1995 | Peterson | 607/5 |
| 5,447,524 A | 9/1995 | Alt | 607/19 |
| 5,456,261 A | 10/1995 | Luczyk | 128/702 |
| 5,458,620 A | 10/1995 | Adams et al. | |
| 5,458,623 A | 10/1995 | Lu et al. | 607/28 |
| 5,466,245 A | 11/1995 | Spinelli et al. | |
| 5,476,482 A | 12/1995 | Lu | 607/9 |
| 5,480,412 A | 1/1996 | Mouchawar et al. | |
| 5,487,754 A | 1/1996 | Snell et al. | |
| 5,496,350 A | 3/1996 | Lu | 607/14 |
| 5,503,159 A | 4/1996 | Burton | 128/703 |
| 5,509,927 A | 4/1996 | Epstein et al. | 607/32 |
| 5,520,191 A | 5/1996 | Karlsson et al. | 128/702 |
| 5,542,430 A | 8/1996 | Farrugia et al. | 128/705 |
| 5,549,641 A | 8/1996 | Ayers et al. | 607/4 |
| 5,551,427 A | 9/1996 | Altman | 128/642 |
| 5,560,368 A | 10/1996 | Berger | |
| 5,571,144 A | 11/1996 | Schroeppel | |
| 5,609,158 A | 3/1997 | Chan | 128/705 |
| 5,628,326 A | 5/1997 | Arand et al. | 128/706 |
| 5,634,468 A | 6/1997 | Platt et al. | 128/696 |
| 5,645,070 A | 7/1997 | Turcott | 128/702 |
| 5,682,900 A | 11/1997 | Arand et al. | |
| 5,683,425 A | 11/1997 | Hauptmann | 607/9 |
| 5,685,315 A | 11/1997 | McClure et al. | |
| 5,687,737 A | 11/1997 | Branham et al. | 128/710 |
| 5,697,377 A | 12/1997 | Witkampf | 128/696 |
| 5,704,365 A | 1/1998 | Albrecht et al. | 128/702 |
| 5,712,801 A | 1/1998 | Turcott | 364/550 |
| 5,713,367 A | 2/1998 | Arnold et al. | 128/704 |
| 5,718,242 A | 2/1998 | McClure et al. | |
| 5,725,561 A | 3/1998 | Stroebel et al. | 607/9 |
| 5,738,105 A | 4/1998 | Kroll | 128/708 |
| 5,749,900 A | 5/1998 | Schroeppel et al. | |
| 5,755,736 A | 5/1998 | Gillberg et al. | 607/4 |
| 5,772,604 A | 6/1998 | Langberg et al. | 600/518 |
| 5,776,072 A | 7/1998 | Hsu et al. | 600/518 |
| 5,779,645 A | 7/1998 | Olson et al. | 600/518 |
| 5,792,065 A | 8/1998 | Xue et al. | 600/516 |
| 5,795,303 A | 8/1998 | Swanson et al. | 600/509 |
| 5,797,399 A | 8/1998 | Morris et al. | 128/705 |
| 5,797,849 A | 8/1998 | Vesely et al. | 600/461 |
| 5,810,739 A | 9/1998 | Bornzin et al. | 600/510 |
| 5,817,133 A | 10/1998 | Houben | 607/9 |
| 5,819,741 A | 10/1998 | Karlsson | |
| 5,827,197 A | 10/1998 | Bocek et al. | 600/518 |
| 5,848,972 A | 12/1998 | Triedman et al. | 600/508 |
| 5,857,977 A | 1/1999 | Caswell et al. | 600/518 |
| 5,858,977 A | 1/1999 | Aukerman et al. | 514/12 |
| 5,868,680 A | 2/1999 | Steiner et al. | 600/518 |
| 5,885,221 A | 3/1999 | Hsu et al. | 600/515 |
| 5,935,082 A | 8/1999 | Albrecht et al. | 600/515 |
| 5,941,831 A | 8/1999 | Turcott | |
| 5,954,661 A | 9/1999 | Greenspon et al. | 600/510 |
| 5,978,700 A | 11/1999 | Nigam | 600/518 |
| 5,983,126 A | 11/1999 | Wittkampf | 600/509 |
| 5,983,138 A | 11/1999 | Kramer | 607/9 |
| 6,016,442 A | 1/2000 | Hsu et al. | 600/518 |
| 6,024,705 A | 2/2000 | Schlager et al. | |
| 6,076,014 A | 6/2000 | Alt | 607/4 |
| 6,096,061 A | 8/2000 | Alt | 607/4 |
| 6,151,524 A | 11/2000 | Krig et al. | |
| 6,179,865 B1 * | 1/2001 | Hsu et al. | 600/518 |
| 6,181,966 B1 | 1/2001 | Nigam | |
| 6,192,273 B1 | 2/2001 | Igel et al. | 607/14 |
| 6,212,428 B1 | 4/2001 | Hsu et al. | |
| 6,216,032 B1 | 4/2001 | Griffin et al. | |
| 6,223,078 B1 | 4/2001 | Marcovecchio | 607/5 |
| 6,224,553 B1 | 5/2001 | Nevo | |
| 6,233,487 B1 | 5/2001 | Mika et al. | |
| 6,253,102 B1 | 6/2001 | Hsu et al. | |
| 6,266,554 B1 | 7/2001 | Hsu et al. | 600/515 |
| 6,269,263 B1 | 7/2001 | Ohnishi et al. | |
| 6,272,377 B1 | 8/2001 | Sweeney et al. | |
| 6,275,732 B1 | 8/2001 | Hsu et al. | 607/14 |
| 6,301,499 B1 | 10/2001 | Carlson et al. | |
| 6,308,095 B1 | 10/2001 | Hsu et al. | 600/518 |
| 6,312,388 B1 | 11/2001 | Marcovecchio et al. | 600/508 |
| 6,314,321 B1 | 11/2001 | Morris | 607/9 |
| 6,317,632 B1 | 11/2001 | Krig et al. | |
| 6,353,759 B1 | 3/2002 | Hartley et al. | 607/9 |
| 6,411,848 B2 | 6/2002 | Kramer et al. | 607/9 |
| 6,430,435 B1 | 8/2002 | Hsu et al. | 600/518 |
| 6,430,438 B1 | 8/2002 | Chen et al. | 607/5 |
| 6,434,417 B1 | 8/2002 | Lovett | 600/509 |
| 6,438,410 B2 | 8/2002 | Hsu et al. | 600/516 |
| 6,442,425 B1 | 8/2002 | Alt | 607/4 |
| 6,449,503 B1 | 9/2002 | Hsu | 600/518 |
| 6,484,055 B1 | 11/2002 | Marcovecchio | |
| 6,516,225 B1 | 2/2003 | Florio | |
| 6,522,917 B1 | 2/2003 | Hsu et al. | 600/518 |
| 6,571,121 B2 | 5/2003 | Schroeppel et al. | |
| 6,571,122 B2 | 5/2003 | Schroeppel et al. | |
| 6,671,548 B1 * | 12/2003 | Mouchawar et al. | 607/14 |
| 6,728,572 B2 | 4/2004 | Hsu et al. | |
| 6,889,081 B2 | 5/2005 | Hsu | |
| 6,922,585 B2 | 7/2005 | Zhou et al. | |
| 6,959,212 B2 | 10/2005 | Hsu et al. | |
| 7,025,730 B2 | 4/2006 | Cho et al. | |
| 7,062,316 B2 | 6/2006 | Hsu et al. | |

|   |   |   |   |
|---|---|---|---|
| 7,203,535 B1 * | 4/2007 | Hsu et al. | 600/518 |
| 2002/0016550 A1 | 2/2002 | Sweeney et al. | |
| 2002/0032469 A1 * | 3/2002 | Marcovecchio | 607/5 |
| 2002/0072683 A1 | 6/2002 | Schroeppel et al. | |
| 2002/0091333 A1 * | 7/2002 | Hsu et al. | 600/518 |
| 2003/0060849 A1 | 3/2003 | Hsu | |
| 2003/0074026 A1 | 4/2003 | Thompson et al. | |
| 2003/0109792 A1 | 6/2003 | Hsu et al. | |
| 2003/0229380 A1 | 12/2003 | Adams et al. | |
| 2004/0093035 A1 | 5/2004 | Schwartz et al. | 607/5 |
| 2004/0172074 A1 | 9/2004 | Yoshihito | |
| 2004/0172075 A1 | 9/2004 | Shafer et al. | |
| 2005/0159781 A1 | 7/2005 | Hsu et al. | |

FOREIGN PATENT DOCUMENTS

|   |   |   |
|---|---|---|
| EP | 0506230 A1 | 9/1992 |
| EP | 0540141 A1 | 5/1993 |
| EP | 0554208 A2 | 8/1993 |
| EP | 0711531 A1 | 5/1996 |
| EP | 0776630 A1 | 11/1996 |
| EP | 0848965 A2 | 6/1998 |
| EP | 0879621 A2 | 11/1998 |
| WO | WO-9406350 A1 | 3/1994 |
| WO | WO-97/39681 A1 | 4/1996 |
| WO | WO-97/39799 A1 | 10/1997 |
| WO | WO-9815319 A1 | 4/1998 |
| WO | WO-98/40010 A1 | 9/1998 |
| WO | WO-98/53879 A1 | 12/1998 |
| WO | WO-9965570 A1 | 12/1999 |
| WO | WO-0047278 A1 | 8/2000 |
| WO | WO-0167948 A2 | 9/2001 |

OTHER PUBLICATIONS

Ellenbogen, Kenneth A., "Cardiac Pacing", Cambridge, Mass., USA : *Blackwell Science*, 2nd ed., (1996),311-312 & 435-437.

Grady, Thomas A., et al., "Prognostice Significance of Exercise-Induced Left Bundle-Branch Block", *JAMA*, vol. 279, No. 2, Jan. 14, 1998, (Jan. 14, 1998),153-156.

Kinoshita, Shinji, et al., "Transient Disappearance of Complete Right Bundle Branch (BBB) During Exercise", *Journal of Electrocardiology*, vol. 29, No. 3, 1996, (1996),225-256.

Lecarpentier, G. L., et al., "Differentiation of sinus tachycardia from ventricular tachycardia with 1:1 ventriculoatrial conduction in dual chamber implantable cardioverter defibrillators: feasibility of a criterion based on atrioventricular interval.", *PACE 1994*; 17(Pt.I), (1994),1818-1831.

Thompson, Julie , "Template Based AV/VA Interval Comparison for the Discrimination of Cardiac Arrhythmia", U.S. Appl. No. 10/844,475, filed May 12, 2004 33 pgs.

Thompson, J A., et al., "Ventriculoatrial conduction metrics for classification of ventricular tachycardia with 1:1 retrograde conduction with dual-chamber sensing implantable cardioverter defibrillators", *J. of Electrocardiography 1998*; 31, (1998),152-156.

Hsu, William, "System and Method for Classifying Tachycardia Arrhythmias Having 1:1 Atrial to Ventricular Rhythms", U.S. Appl. No. 09/417,588, filed on Oct. 13, 1999, 39 pgs.

Stadler, Robert W., et al., "An Adaptive Interval-Based Algorithm for Withholding ICD Therapy During Sinus Tachycardia", *PACE*, vol. 26, (2003), 1189-1201.

"U.S. Appl. No. 09/248,800 Amendment Under 37 CFR 1.312 filed Jul. 17, 2001", 5 pgs.

"U.S. Appl. No. 09/248,800 Final Office Action mailed Dec. 12, 2000", 7 pgs.

"U.S. Appl. No. 09/248,800 Non Final Office Action mailed Mar. 29, 2000", 9 pgs.

"U.S. Appl. No. 09/248,800 Notice of Allowance mailed Apr. 17, 2001", 3 pgs.

"U.S. Appl. No. 09/248,800 Response filed Mar. 22, 2001 to Final Office Action mailed Dec. 22, 2000", 10 pgs.

"U.S. Appl. No. 09/248,800 Response filed Jun. 29, 2000 to Non Final Office Action Mailed Mar. 29, 2000", 11 pgs.

"U.S. Appl. No. 10/014,933 Non Final Office Action mailed Nov. 14, 2003", 7 pgs.

"U.S. Appl. No. 10/014,933 Notice of Allowance mailed Feb. 6, 2004", 4 pgs.

"U.S. Appl. No. 10/014,933 Notice of Allowance mailed Apr. 22, 2005", 5 pgs.

"U.S. Appl. No. 10/014,933 Response filed Jan. 16, 2004 to Non Final Office Action mailed Nov. 14, 2003", 10 pgs.

"U.S. Appl. No. 10/014,933 Response filed Jan. 16, 2004 to Non Final Office Action mailed Nov. 14, 2003", 10 pgs.

* cited by examiner

TEMPLATE BASED AV/VA INTERVAL COMPARISON FOR THE DISCRIMINATION OF CARDIAC ARRHYTHMIAS

CROSS-REFERENCE TO RELATED APPLICATIONS

This application is related to commonly assigned U.S. Pat. No. 6,959,212 entitled "SYSTEM AND METHOD FOR ARRHYTHMIA DISCRIMINATION," filed on Oct. 22, 2001, U.S. Pat. No. 6,889,081 entitled "CLASSIFICATION OF SUPRAVENTRICULAR AND VENTRICULAR CARDIAC RHYTHMS USING CROSS CHANNEL TIMING ALGORITHM," filed on Jul. 23, 2002, U.S. Pat. No. 6,728,572 application Ser. No. 10/219,730, entitled "SYSTEM AND METHOD FOR CLASSIFYING CARDIAC COMPLEXES," filed on Aug. 14, 2002, and U.S. Pat. No. 7,062,316 entitled "CROSS CHANNEL INTERVAL CORRELATION," filed on Jan. 21, 2003, which are hereby incorporated by reference in their entirety.

TECHNICAL FIELD

This document relates generally to cardiac rhythm management (CRM) systems and particularly, but not by way of limitation, to such a system providing for discrimination of ventricular tachycardia (VT) from supraventricular tachycardia (SVT) based on analysis of time intervals between atrial and ventricular depolarizations.

BACKGROUND

The heart is the center of a person's circulatory system. The left portions of the heart, including the left atrium (LA) and left ventricle (LV), draw oxygenated blood from the lungs and pump it to the organs of the body to provide the organs with their metabolic needs for oxygen. The right portions of the heart, including the right atrium (RA) and right ventricle (RV), draw deoxygenated blood from the body organs and pump it to the lungs where the blood gets oxygenated. These mechanical pumping functions are accomplished by contractions of the heart. In a normal heart, the sinoatrial (SA) node, the heart's natural pacemaker, generates electrical impulses, called action potentials, that propagate through an electrical conduction system to various regions of the heart to cause the muscular tissues of these regions to depolarize and contract. The electrical conduction system includes, in the order by which the electrical impulses travel in a normal heart, internodal pathways between the SA node and the atrioventricular (AV) node, the AV node, the His bundle, and the Purkinje system including the right bundle branch (RBB, which conducts the electrical impulses to the RV) and the left bundle branch (LBB, which conducts the electrical impulses to the LV). More generally, the electrical impulses travel through an AV conduction pathway to cause the atria, and then the ventricles, to contract.

Tachycardia (also referred to as tachyarrhythmia) occurs when the heart contracts at a rate higher than a normal heart rate. Tachycardia generally includes ventricular tachycardia (VT) and supraventricular tachycardia (SVT). VT occurs, for example, when a pathological conduction loop formed in the ventricles through which electrical impulses travel circularly within the ventricles, or when a pathologically formed electrical focus generates electrical impulses from the ventricles. SVT includes physiologic sinus tachycardia and pathologic SVTs. The physiologic sinus tachycardia occurs when the SA node generates the electrical impulses at a particularly high rate. A pathologic SVT occurs, for example, when a pathologic conduction loop forms in an atrium. Fibrillation occurs when the heart contracts at a tachycardia rate with an irregular rhythm. Ventricular fibrillation (VF), as a ventricular arrhythmia with an irregular conduction, is a life threatening condition requiring immediate medical treatment such as ventricular defibrillation. Atrial fibrillation (AF), as a SVT with an irregular rhythm, though not directly life threatening, also needs medical treatment such as atrial defibrillation to restore a normal cardiac function and prevents the deterioration of the heart.

Implantable cardioverter/defibrillators (ICDs) are used to treat tachycardias, including fibrillation. To deliver an effective cardioversion/defibrillation therapy, the cardioversion/defibrillation energy is to be delivered to the chambers of the heart where the tachycardia or fibrillation originates. When the atrial rate of depolarizations (or contractions) is substantially different from the ventricular rate of depolarizations (or contractions), the atrial and ventricular rates of depolarizations (or contractions) provide for a basis for locating where the tachycardia originates. However, there is a need to locate where the tachycardia originates when the atrial depolarizations and the ventricular depolarizations present a one-to-one (1:1) relationship.

SUMMARY

An implantable cardioverter/defibrillator includes a tachycardia detection system that detects 1:1 tachycardia, which is a tachycardia with the 1:1 relationship between atrial and ventricular contractions. When the 1:1 tachycardia is detected, the system locates where the tachycardia originates by discriminating VT from SVT based on analysis of a cardiac time interval. Examples of the cardiac time interval include an atrioventricular interval (AVI) and a ventriculoatrial interval (VAI).

In one embodiment, a system for discriminating VT from SVT includes a sensing circuit, a rate detector circuit, a tachycardia detector circuit, a rhythm classifier circuit, and a tachycardia discriminator circuit. The sensing circuit senses an atrial electrogram indicative of atrial depolarizations and a ventricular electrogram indicative of ventricular depolarizations. The rate detector circuit detects an atrial rate based on the atrial electrogram and a ventricular rate based on the ventricular electrogram. The tachycardia detector circuit detects a tachycardia based on at least one of the atrial rate and the ventricular rate. The rhythm classifier circuit classifies the detected tachycardia as a 1:1 tachycardia when the atrial rate and the ventricular rate are substantially equal. The tachycardia discriminator circuit includes a time interval measurement circuit and a VT comparator circuit. The time interval measurement circuit measures a tachycardia time interval between an atrial depolarization and an adjacent ventricular depolarization during the 1:1 tachycardia. The VT comparator circuit has an output indicating a VT detection when the tachycardia time interval differs from a template time interval by at least a predetermined margin.

In one embodiment, a CRM system includes implantable atrial and ventricular leads coupled to an implantable ICD. The implantable atrial lead allows for sensing an atrial electrogram indicative of atrial depolarizations. The implantable ventricular lead allows for sensing a ventricular electrogram indicative of ventricular depolarizations. The ICD includes a sensing circuit, a rate detector circuit, a tachycardia detector circuit, a rhythm classifier circuit, and a tachycardia discriminator circuit. The sensing circuit is coupled to the implantable atrial lead and the implantable ventricular lead to sense the atrial electrogram and the ventricular electrogram. The rate detector circuit detects an atrial rate based on the atrial electrogram and a ventricular rate based on the ventricular electrogram. The tachycardia detector circuit detects a tachycardia based on at least one of the atrial rate and the ventricular rate. The rhythm classifier circuit classifies the detected tachycardia as a 1:1 tachycardia when the atrial rate and the ventricular rate are substantially equal. The tachycardia discriminator circuit includes a time interval measurement circuit and a VT comparator circuit. The time interval measurement circuit measures a tachycardia time interval between an atrial depolarization and an adjacent ventricular depolarization during the 1:1 tachycardia. The VT comparator circuit has an output indicating a detection of VT when the tachycardia time interval differs from a template time interval by at least a predetermined margin and an SVT detection when the tachycardia time interval does not differ from the template time interval by at least the predetermined margin.

In one embodiment, a method is provided for discriminating VT from SVT. A ventricular rate, or a frequency of ventricular depolarizations, is detected. An atrial rate, or a frequency of atrial depolarizations, is detected. A tachycardia is detected based on at least one of the atrial and ventricular rates. The tachycardia is classified as a 1:1 tachycardia if the detected atrial rate is substantially the same as the detected ventricular rate. A tachycardia time interval is measured between adjacent atrial and ventricular depolarizations during the 1:1 tachycardia. If the tachycardia time interval differs from a template time interval by at least a predetermined margin, a VT detection is indicated.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their equivalents.

BRIEF DESCRIPTION OF THE DRAWINGS

The drawings, which are not necessarily drawn to scale, illustrate generally, by way of example, but not by way of limitation, various embodiments discussed in the present document.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description provides examples, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this documents and those documents so incorporated by reference, the usage in the incorporated reference(s) should be considered supplementary to that of this document; for irreconcilable inconsistencies, the usage in this document controls.

It should be noted that references to "an", "one", or "various" embodiments in this disclosure are not necessarily to the same embodiment, and such references contemplate more than one embodiment.

This document discusses, among other things, a CRM system including a system for discriminating VT from SVT when a 1:1 tachycardia is detected. The 1:1 tachycardia, characterized by a one-to-one association between atrial and ventricular depolarizations, is indicated by a substantially equal atrial rate and ventricular rate. A VT detection is indicated when a cardiac time interval measured during the 1:1 tachycardia differs from a template time interval by at least a predetermined percentage of the template time interval. An SVT detection is indicated when the cardiac time interval measured during the 1:1 tachycardia does not differ from the template time interval by at least the predetermined percentage of the template time interval. The cardiac time interval includes one of an AVI and a VAI. The AVI is the time interval between an atrial depolarization and an adjacently subsequent ventricular depolarization, where the atrial depolarization and the adjacently subsequent ventricular depolarizations are caused by the same electrical impulse traveling through the AV conduction pathway. The VAI is the time interval between a ventricular depolarization and the next atrial depolarization, where the ventricular depolarization is caused by one electrical impulse and the next atrial depolarization is caused by the next electrical impulse.

The percentage of the template time interval represents a limit within which AVI or VAI changes when SVT occurs. The length of AVI in a normal AV conduction pathway is bounded by physiological constraints. There is a physical limit on the conduction speed at which action potentials may propagate through the AV conduction pathway in the normal antegrade direction. During SVT, electrical impulses originate in a supraventricular region and generally propagate through the AV conduction pathway. Sinus tachycardia is associated with a decrease in AVI, and pathologic SVTs are often associated with an increase in AVI. Such decrease and increase in AVI are bounded by a limit that can be measured as a percentage of a template AVI measured during a normal sinus rhythm (NSR). During VT, electrical impulses travel along paths other than the normal AV conduction pathway. The change in AVI during VT is no longer bounded by the limit that applies to the change in AVI during the SVTs. This limit is statistically determined based on a patient population and, in one embodiment, expressed as the percentage of the template AVI. VAI is a known function of AVI, i.e., the difference between the measurable cardiac cycle length (heart rate interval) and the AVI. Therefore, VAI is a readily usable alternative to AVI for the purpose of discriminating VT from SVT.

Figure 1:
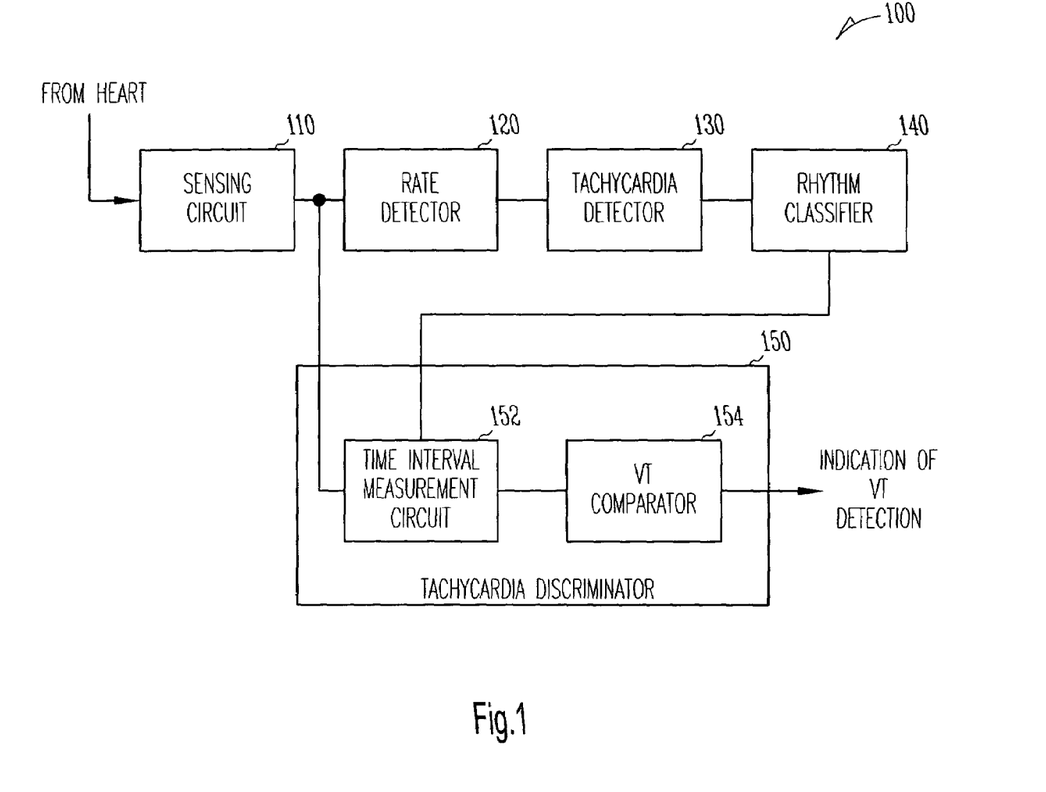
FIG. 1 is a block diagram illustrating an embodiment of a system for discriminating VT from SVT.

FIG. 1 is a block diagram illustrating an embodiment of a system 100 for discriminating VT from SVT. System 100 includes a sensing circuit 110, a rate detector 120 circuit, a tachycardia detector 130 circuit, a rhythm classifier 140 circuit, and a tachycardia discriminator 150 circuit. Sensing circuit 110 is electrically coupled to a heart to sense an atrial electrogram and a ventricular electrogram from the heart. The atrial electrogram includes detectable atrial events, also known as P waves, each indicative of an atrial depolarization. The ventricular electrogram includes detectable ventricular events, also known as R waves, each indicative of a ventricular depolarization. Rate detector 120 detects an atrial rate based on the atrial electrogram and a ventricular rate based on the ventricular electrogram. The atrial rate is the frequency of the atrial events. The ventricular rate is the frequency of the ventricular events. In one embodiment, the atrial and ventricular rates are each expressed in beats per minute (bpm), i.e., number of detected atrial or ventricular depolarizations per minute. Tachycardia detector 130 detects a tachycardia based on at least one of the atrial rate and the ventricular rate. In one embodiment, the tachycardia is detected when the atrial rate exceeds a predetermined tachycardia threshold rate. In another embodiment, the tachycardia is detected when the ventricular rate exceeds a predetermined tachycardia threshold rate. Rhythm classifier 140 classifies the detected tachycardia as a 1:1 tachycardia when the atrial rate and the ventricular rate are substantially equal. In one embodiment, rhythm classifier 140 classifies the detected tachycardia as the 1:1 tachycardia when the difference between the atrial rate and the ventricular rate is between a predetermined limit, such as 10 bpm. Tachycardia discriminator 150 includes a time interval measurement circuit 152 and a VT comparator 154 circuit. Time interval measurement circuit 152 measures a tachycardia time interval during the 1:1 tachycardia, i.e., immediately after the tachycardia is detected and the 1:1 tachycardia is classified. This time interval provides for a quantitative indication of whether the detected tachycardia is VT or SVT. VT comparator 154 includes an output indicating a VT detection when the tachycardia time interval differs from a template time interval by at least a predetermined margin. In one embodiment, the template time interval is the corresponding time interval measured during a known NSR. In one further embodiment, the predetermined margin is at least a predetermined percentage of the template time interval. In one specific embodiment, the time interval is the AVI. The tachycardia time interval is a tachycardia AVI measured during the 1:1 tachycardia. The template time interval is a template AVI measured during the known NSR. VT comparator 154 indicates the VT detection when the tachycardia AVI exceeds the template AVI by a predetermined AVI margin. The predetermined AVI margin is a percentage of the template AVI statistically determined based on a patient population to distinguish VT from SVT. In another specific embodiment, the time interval is a VAI. The tachycardia time interval is a tachycardia VAI measured during the 1:1 tachycardia. The template time interval is a template VAI measured during the known NSR. VT comparator 154 indicates the VT detection when the template VAI exceeds the tachycardia VAI by a predetermined VAI margin, where the template VAI and/or the tachycardia VAI are adjusted for the heart rate. The predetermined VAI margin is a percentage of the template VAI statistically determined based on a patient population to distinguish VT from SVT.

Figure 2:
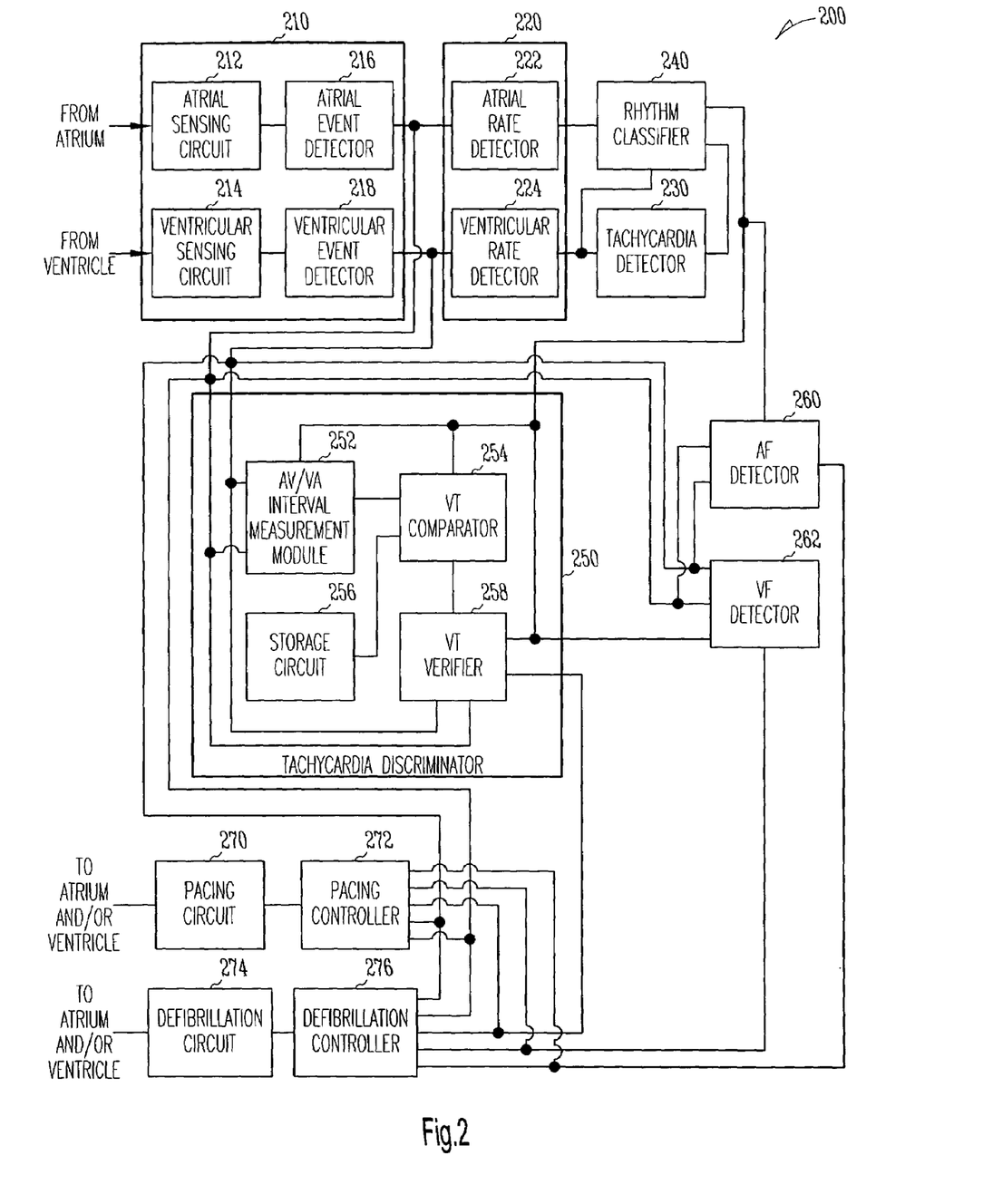
FIG. 2 is a block diagram illustrating a specific embodiment of the system for discriminating VT from SVT.

FIG. 2 is a block diagram illustrating system 200, which represents a specific embodiment of system 100. System 200 includes a sensing circuit 210, a rate detector 220 circuit, a tachycardia detector 230 circuit, a rhythm classifier 240 circuit, a tachycardia discriminator 250 circuit, an AF detector 260 circuit, a VF detector 262 circuit, a pacing circuit 270, a pacing controller 272 circuit, a defibrillation circuit 274, and a defibrillation controller 276 circuit. Sensing circuit 210 includes an atrial sensing circuit 212, a ventricular sensing circuit 214, an atrial event detector 216 circuit, and a ventricular event detector 218 circuit. Atrial sensing circuit 212 is electrically coupled to an atrium of a heart through an atrial pacing-sensing lead to sense the atrial electrogram. Ventricular sensing circuit 214 is electrically coupled to a ventricle of a heart through a ventricular pacing-sensing lead to sense the ventricular electrogram. Atrial event detector 216 receives the sensed atrial electrogram from atrial sensing circuit 212 and detects the atrial events from the atrial electrogram. Ventricular event detector 218 receives the sensed ventricular electrogram from ventricular sensing circuit 214 and detects the ventricular events from the ventricular electrogram.

Rate detector circuit 220 includes an atrial rate detector 222 circuit and a ventricular rate detector 224 circuit. Atrial rate detector 222 detects the atrial rate by calculating the frequency of atrial event detections. In one embodiment, atrial rate detector 222 detects the atrial rate as the number of atrial events detected over a minute. Ventricular rate detector 224 detects the ventricular rate by calculating the frequency of atrial event detections. In one embodiment, ventricular rate detector 224 detects the ventricular rate as the number of ventricular events detected over a minute.

Tachycardia detector 230 detects tachycardia when the ventricular rate exceeds a tachycardia threshold rate. In one embodiment, the tachycardia threshold rate is programmable in a range between 90 bpm and 220 bpm. Tachycardia detector 230 includes a tachycardia comparator circuit having a heart rate input to receive the ventricular rate, a tachycardia threshold input representative of the tachycardia threshold rate, and a tachycardia output indicating that the tachycardia is detected when the ventricular rate exceeds the tachycardia threshold rate.

Rhythm classifier 240 receives the atrial rate from atrial rate detector 222 and the ventricular rate from ventricular rate detector 224. After tachycardia detector 230 indicates that the tachycardia is detected, rhythm classifier 240 classifies the tachycardia as one of VT, SVT, and 1:1 tachycardia. In one embodiment, rhythm classifier 240 includes a rhythm comparator circuit to compare the atrial rate to the ventricular rate after the tachycardia is detected. The rhythm comparator has an atrial rate input to receive the atrial rate, a ventricular rate input to receive a ventricular rate, and a classification output indicative of VT if the ventricular rate is substantially higher than the atrial rate. The classification output is indicative of SVT if the atrial rate is substantially higher than the ventricular rate, and is indicative of 1:1 tachycardia if the atrial rate and the ventricular rate are substantially equal. In one embodiment, the classification output is indicative of SVT or dual arrhythmia if the atrial rate is substantially higher than the ventricular rate. The dual arrhythmia includes concurrent VT and SVT, and the SVT causes an atrial rate that is higher than the ventricular rate caused by the VT. If rhythm classifier 240 classifies the tachycardia as SVT or dual arrhythmia, further detection is performed to determine whether the detected tachycardia is AVT or concurrent SVT and VT.

Tachycardia discriminator 250 detects VT by discriminating VT from SVT when 1:1 tachycardia is detected by rhythm classifier 240. In one embodiment, tachycardia discriminator 250 includes an AV/VA interval measurement module 252, a VT comparator 254 circuit, a storage circuit 256, and a VT verifier 258 circuit. After the tachycardia is detected and classified as the 1:1 tachycardia, AV/VA interval measurement module 252 measures at least one of the tachycardia AVI and the tachycardia VAI. The tachycardia AVI is a time interval measured between a detected atrial event and a successively detected ventricular event during the 1:1 tachycardia. The tachycardia VAI is a time interval measured between a detected ventricular event and a successively detected atrial event during the 1:1 tachycardia. In one embodiment, in which only the tachycardia AVI is measured, AV/VA interval measurement module 252 is an AVI measurement module. In another embodiment, in which only the tachycardia VAI is measured, AV/VA interval measurement module 252 is a VAI measurement module. VT comparator 254 has a tachycardia time interval input to receive the tachycardia AVI or VAI, a VT threshold interval input to receive the corresponding VT template time interval offset by at least a predetermined percentage of the template time interval, and an output indicating a VT detection when the tachycardia AVI or VAI differs from the corresponding VT template time interval by at least the predetermined percentage of the template time interval. In one embodiment, the tachycardia time interval input receives the tachycardia AVI, the VT threshold interval input receives a VT threshold AVI, and the VT output indicates that VT is detected when the tachycardia AVI exceeds VT threshold AVI, which is the template AVI plus at least a predetermined percentage of the template AVI. In another embodiment, the tachycardia time interval input receives the tachycardia VAI, the VT threshold interval input receives a VT threshold VAI, and the VT output indicates that VT is detected when the tachycardia VAI differs from the VT threshold VAI, which is the template VAI, by at least a predetermined percentage of the template VAI. In one embodiment, the tachycardia VAI received by the tachycardia time interval input is adjusted for the heart rate based on a tachycardia heart rate measured during the 1:1 tachycardia and the heart rate at which the template VAI was measured. If as the result of comparison, VT comparator 254 does not indicate that VT is detected, it indicates that SVT is detected. Storage circuit 256 stores the template AVI and/or VAI. In one embodiment, the template AVI and/or VAI are measured by AV/VA interval measurement module during the known NSR and stored in storage circuit 256. In one further embodiment, a template heart rate is measured, such as by atrial rate detector 222 or ventricular rate detector 224, during the known NSR and stored in storage circuit 256. At least the predetermined percentage associated with the template AVI and/or at least the predetermined percentage associated with the template VAI are programmed into storage circuit 256. In one embodiment, tachycardia discriminator 250 indicates the VT or SVT detection only after the result of comparison by VT comparator 254 is verified by VT verifier 258. VT verifier 258 applies at least one different method to detect VT. In one embodiment, VT verifier 258 includes another tachycardia discriminator circuit that discriminates VT from SVT after the tachycardia is classified as the 1:1 tachycardia. This tachycardia discriminator uses a method for discriminating VT from SVT that is different from the method used by tachycardia discriminator 250. Examples of tachycardia discriminators using different methods for discriminating VT from SVT are discussed in U.S. Pat. No. 6,449,503, entitled "CLASSIFICATION OF SUPRAVENTRICULAR AND VENTRICULAR CARDIAC RHYTHMS USING CROSS CHANNEL TIMING ALGORITHM," U.S. Pat. No. 6,179,865, entitled "CROSS CHANNEL INTERVAL CORRELATION," U.S. Pat. No. 6,275,732, entitled "MULTIPLE STAGE MORPHOLOGY-BASED SYSTEM DETECTING VENTRICULAR TACHYCARDIA AND SUPRAVENTRICULAR TACHYCARDIA," and U.S. Pat. No. 6,308,095, entitled "SYSTEM AND METHOD FOR ARRHYTHMIA DISCRIMINATION," all assigned to Cardiac Pacemakers, Inc., which are incorporated by reference in their entirety. These examples are intended for illustrative purpose only and not intended to be a complete or extensive list of potentially useable apparatuses and methods.

In one embodiment, AF detector 260 detects AF, in addition to the SVT classification by rhythm classifier 240 and the SVT detection by tachycardia discriminator 250. In one embodiment, VF detector 262 detects VF, in addition to the VT detection by rhythm classifier 240 and the VT detection by tachycardia discriminator 250.

Pacing circuit 270 delivers pacing pulses to the heart. Pacing controller 272 controls the delivery of the pacing pulses. Defibrillation circuit 274 delivers cardioversion/defibrillation shocks to the heart. Defibrillation controller 276 controls delivery of the cardioversion/defibrillation shocks. In one embodiment, pacing controller 272 provides for control of delivery of an anti-tachycardia pacing (ATP) therapy in response to a VT or VF detection. In one embodiment, defibrillation circuit 274 includes an atrial defibrillation circuit to deliver atrial cardioversion/defibrillation shocks through an atrial defibrillation lead having at least one defibrillation electrode disposed in a supraventricular region. Defibrillation controller 276 includes an atrial defibrillation controller providing for control of delivery of an atrial cardioversion/defibrillation therapy in response to an SVT or AF detection. In another embodiment, defibrillation circuit 274 includes a ventricular defibrillation circuit to deliver ventricular cardioversion/defibrillation shocks through a ventricular defibrillation lead having at least one defibrillation electrode disposed in or near a ventricular region. Defibrillation controller 276 includes a ventricular defibrillation controller providing for control of delivery of a ventricular cardioversion/defibrillation therapy in response to a VT or VF detection.

Figure 3:
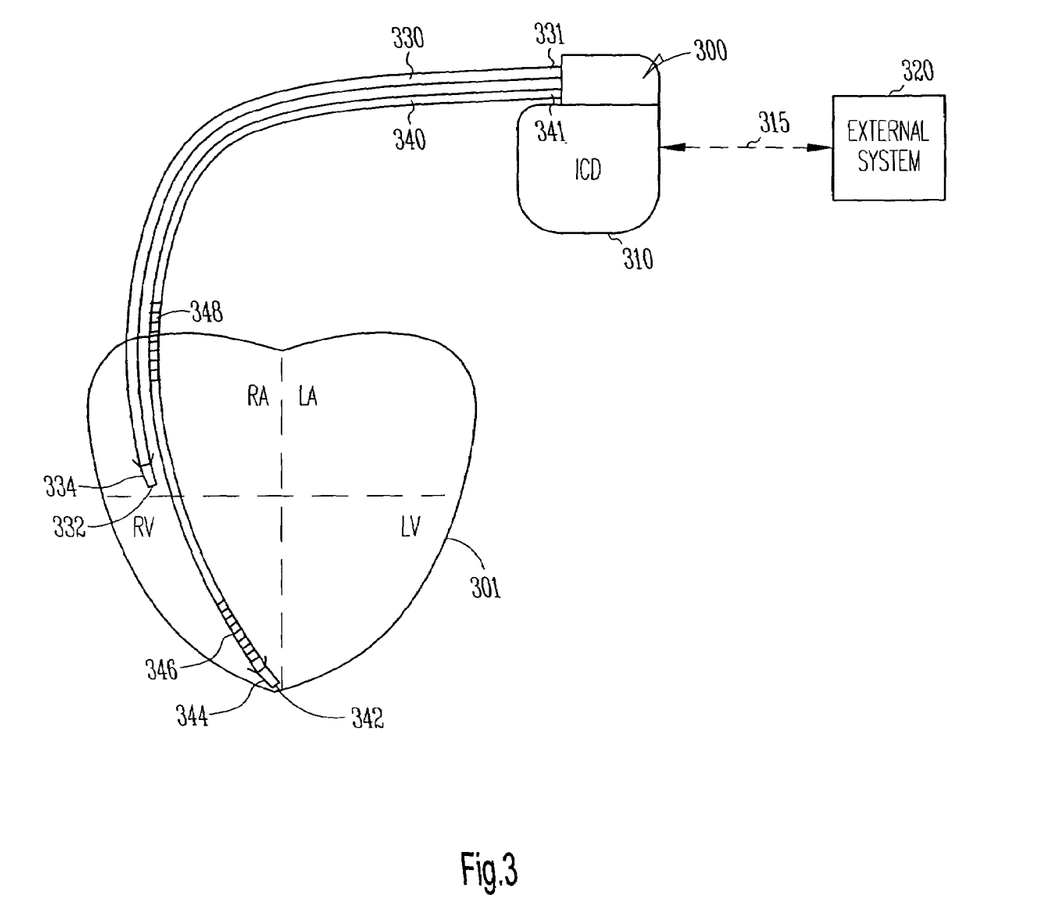
FIG. 3 is an illustration a CRM system including an ICD and portions of the environment in which the CRM system operates.

FIG. 3 is an illustration of a CRM system including an ICD 310 and portions of the environment in which the CRM system operates. The CRM system includes an implantable system 300, an external system 320, and a telemetry link 315 providing for bidirectional communication between implantable system 300 and external system 320. Implantable system 300 includes ICD 310, which is electrically coupled to a heart 301 via at least a pacing lead 330 and a defibrillation lead 340.

ICD 310 includes a hermetically sealed can to house electronics including a tachycardia detection system such as system 100 or system 200 discussed above. The hermetically sealed can also functions as an electrode for pacing, sensing, and/or defibrillation purposes. Pacing lead 330 includes a proximal end 331 connected to ICD 310 and a distal end 332 disposed in the RA. A pacing-sensing electrode 334 at or near distal end 332 is electrically connected to the sensing circuit of system 100 or 200 to allow the atrial electrogram sensing and delivery of atrial pacing pulses. Defibrillation lead 340 includes a proximal end 341 connected to ICD 310 and a distal end 342 disposed in the RV. A pacing-sensing electrode 344 at or near distal end 342 is electrically connected to the sensing circuit of system 100 or 200 to allow the ventricular electrogram sensing and delivery of ventricular pacing pulses. A first defibrillation electrode 346 near distal end 342 but electrically separated from pacing-sensing electrode 344 is electrically connected to defibrillation circuit 274 to allow delivery of cardioversion/defibrillation shocks to a ventricular region. A second defibrillation electrode 348, located at a distance from distal end 342 for supraventricular placement, is electrically connected to defibrillation circuit 274 to allow delivery of cardioversion/defibrillation shocks to a supraventricular region.

External system 320 provides for access to implantable system 300 for purposes such as programming ICD 310 and receiving signals acquired by ICD 310. In one embodiment, external system 320 includes a programmer. In another embodiment, external system 320 is a patient management system including an external device in proximity of ICD 310, a remote device in a relatively distant location, and a telecommunication network linking the external device and the remote device. The patient management system allows access to implantable system 300 from a remote location, for purposes such as monitoring patient status and adjusting therapies. In one embodiment, telemetry link 315 is an inductive telemetry link. In an alternative embodiment, telemetry link 315 is a far-field radio-frequency telemetry link. In one embodiment, telemetry link 315 provides for data transmission from ICD 310 to external system 320. This may include, for example, transmitting real-time physiological data acquired by ICD 310, extracting physiological data acquired by and stored in ICD 310, extracting therapy history data stored in ICD 310, and extracting data indicating an operational status of ICD 300 (e.g., battery status and lead impedance). In a further embodiment, telemetry link 315 provides for data transmission from external system 320 to ICD 310. This may include, for example, programming ICD 310 to acquire physiological data, programming ICD 310 to perform at least one self-diagnostic test (such as for a device operational status), programming ICD 310 to run an data analysis algorithm (such as an algorithm implementing the tachycardia detection methods discussed in this document), and programming ICD 310 to deliver at least one therapy.

Figure 4:
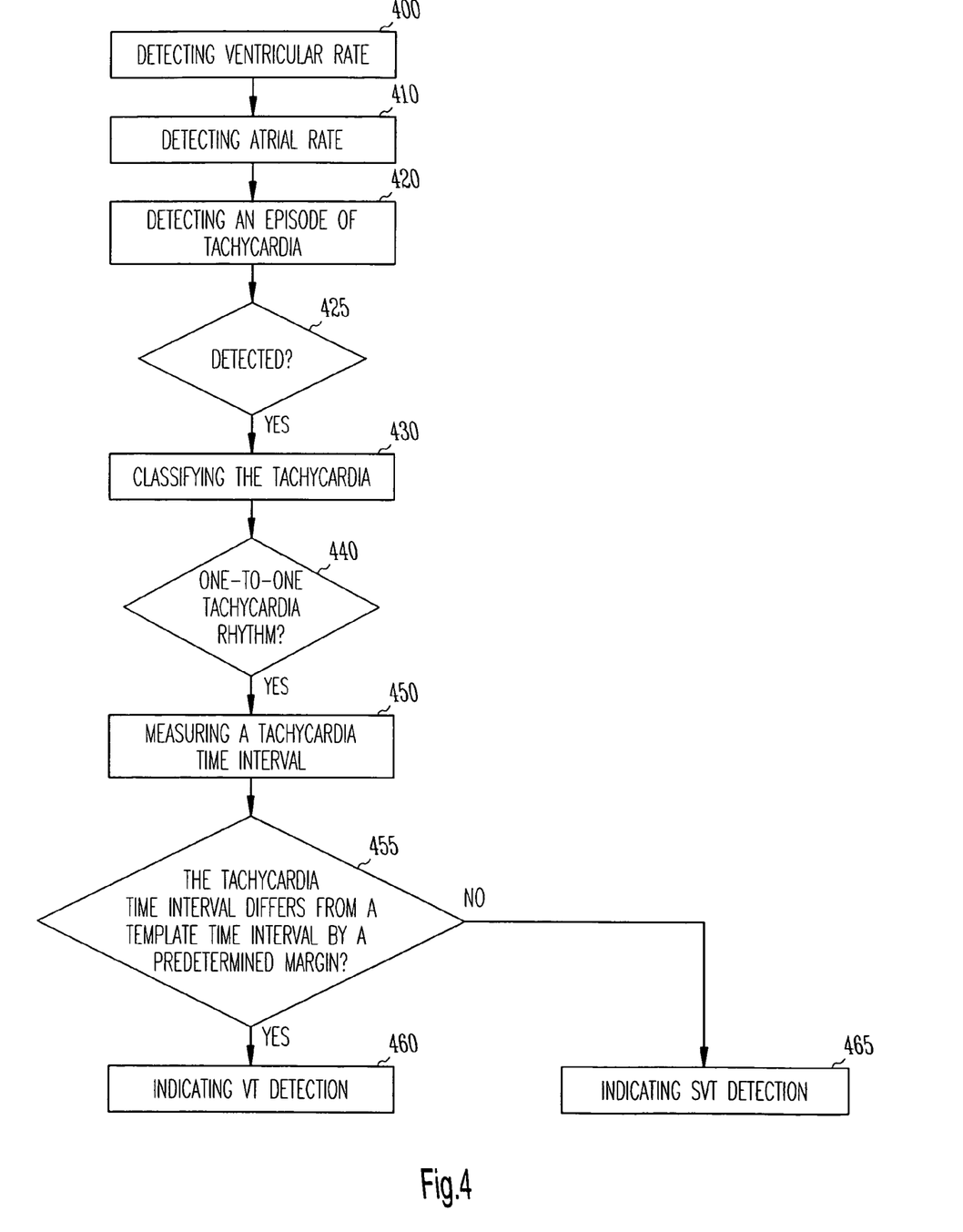
FIG. 4 is a flow chart illustrating an embodiment of a method for discriminating VT from SVT.

FIG. 4 is a flow chart illustrating an embodiment of a method for discriminating VT from SVT. A ventricular rate is detected at 400, where the ventricular rate is the frequency of ventricular depolarizations. An atrial rate is detected at 410, where the atrial rate is the frequency of atrial depolarizations. A tachycardia is being detected based on at least one of the atrial and ventricular rates at 420. If the episode of tachycardia is detected at 425, the tachycardia is classified at 430. If the detected atrial rate substantially equals the detected ventricular rate, the detected tachycardia is classified as a 1:1 tachycardia. If the detected tachycardia is classified as a 1:1 tachycardia at 440, a tachycardia time interval is measured between adjacent atrial and ventricular depolarizations at 450, during the 1:1 tachycardia. The tachycardia time interval is compared with a template time interval to determine whether it differs from the template time interval by at least a predetermined margin at 455. In one embodiment, the margin is determined as a percentage of the template time interval based on a statistical study with a patient population. In another embodiment, the margin is determined for a patient as a percentage of the template time interval based on measurements performed individually with that patient. If the tachycardia time interval differs from the template time interval by the predetermined margin at 455, a VT detection is indicated at 460. If the tachycardia time interval does not differ from the template time interval by the predetermined margin at 455, an SVT detection is indicated at 465.

Figure 5:
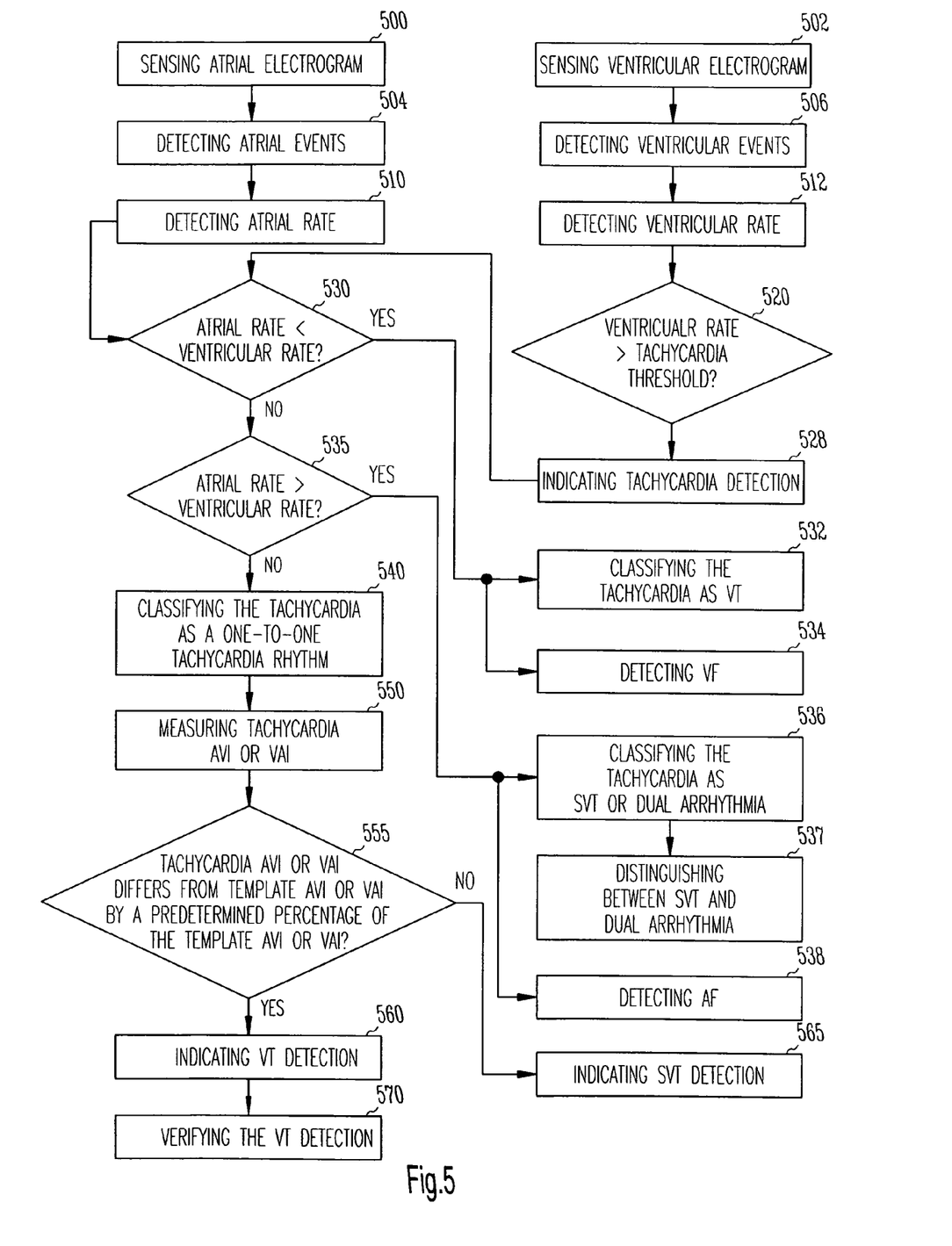
FIG. 5 is a flow chart illustrating a specific embodiment of the method for discriminating VT from SVT.

FIG. 5 is a flow chart illustrating a specific embodiment of the method for discriminating VT from SVT that is illustrated in FIG. 4. An atrial electrogram is sensed at 500. A ventricular electrogram is sensed at 502. Atrial events, or P waves, are detected from the atrial electrogram at 504. Ventricular events, or R waves, are detected from the ventricular electrogram at 506. The atrial rate is detected at 510. The ventricular rate is detected at 512.

Tachycardia detection is performed by comparing the ventricular rate to a tachycardia threshold rate at 520. If the detected ventricular rate exceeds the tachycardia threshold rate at 520, a tachycardia detection is indicated at 528. In one embodiment, the tachycardia threshold rate is programmable in a range between 90 bpm and 220 bpm.

After being detected, the tachycardia is classified as one of VT, SVT, and 1:1 tachycardia based on a comparison between the detected atrial rate and the detected ventricular rate. If the detected atrial rate is lower than the detected ventricular rate at 530, the tachycardia is classified as VT at 532. In one embodiment, the tachycardia is classified as VT if the detected atrial rate is lower than the detected ventricular rate by at least a predetermined margin. In one specific embodiment, the predetermined margin is about 10 bpm. In one embodiment, VF detection is performed at 534, in addition to any VT classification. In one further embodiment, at least one ventricular defibrillation shock is delivered immediately in response to any VF detection. If the detected atrial rate is higher than the detected ventricular rate at 535, the tachycardia is classified as SVT or dual arrhythmia at 536. In one embodiment, the tachycardia is classified as SVT or dual arrhythmia if the detected atrial rate is higher than the detected ventricular rate by at least a predetermined margin. In one specific embodiment, the predetermined margin is about 10 bpm. In one embodiment, a further detection is performed to distinguish between SVT and dual arrhythmia at 537. The result of this further detection determines whether the tachycardia is classified as SVT or VT. In one embodiment, AF detection is performed at 538, in addition to any SVT classification. In one further embodiment, at least one atrial defibrillation shock is delivered in response to an AF detection. If the detected atrial rate is neither lower nor higher than the detected ventricular rate, the tachycardia is classified as the 1:1 tachycardia at 540. In one embodiment, the tachycardia is classified as the 1:1 tachycardia if the detected atrial rate is neither lower than the detected ventricular rate by the predetermined margin nor higher than the detected ventricular rate by the predetermined margin. That is, the tachycardia is classified as the 1:1 tachycardia if the difference between the detected atrial rate and the detected ventricular rate is within a predetermined window.

If tachycardia is classified as the 1:1 tachycardia at 540, a tachycardia AVI and/or a tachycardia VAI are measured at 550. VT is detected by discriminating VT from SVT based on a comparison between a template AVI and the tachycardia AVI and/or a comparison between a template VAI and the tachycardia VAI. The template AVI is created by an AVI during a known NSR. The template VAI is created by a VAI during a known NSR. If the tachycardia AVI differs from the template AVI by at least a predetermined percentage of the template AVI, and/or if the tachycardia VAI differs from the template VAI by at least a predetermined percentage of the template VAI, a VT detection is indicated at 560; otherwise, an SVT detection is indicated at 565. The percentage is determined based on a statistical analysis based on a patient population. The statistical analysis results in an AVI limit to which the AVI may change from its NSR value (the template AVI) during an SVT and/or an VAI limit to which the VAI may change from its NSR value (the template VAI) during an SVT. VT is indicated if the difference from measured tachycardia AVI and the template AVI exceeds the AVI limit, and/or if the difference from measured tachycardia VAI and the template VAI exceeds the VAI limit, where the template VAI and/or the tachycardia VAI are adjusted for the heart rate. The AVI limit is expressed as a percentage of the template AVI. The VAI limit is expressed as a percentage of the template VAI.

In one embodiment, after being indicated at 560, the VT detection is verified at 570 by applying a different method for discriminating VT from SVT after a classification of 1:1 tachycardia. Examples of the different methods are discussed in U.S. Pat. Nos. 6,449,503, 6,179,865, 6,275,732, and 6,308,095, as discussed above. In another embodiment, one of these different methods for discriminating VT from SVT is used as the primary method of discriminating VT from SVT after a classification of 1:1 tachycardia, and the method illustrated in FIG. 4 or 5 is used for verification.

Discrimination of VT from SVT can be performed using variations of the embodiments discussed above without deviating from the concepts embedded in these embodiments. In one embodiment, the limit to the cardiac time interval, such as the AVI limit or the VAI limit, is expressed as a ratio or other amount, instead of the percentage of the template time interval. In another embodiment, the ratio of the tachycardia time interval to the template time interval is compared to a predetermined ratio for discriminating VT from SVT. In one embodiment, atrial and ventricular intervals, instead of the atrial and ventricular rates, are detected and used for the tachycardia detection and classification. The relationship between a rate and an interval, as used in this document, is the relationship between a frequency and its corresponding period. If a rate is given in beats per minute (bpm), its corresponding interval in millisecond is calculated by dividing 60,000 by the rate (where 60,000 is the number of milliseconds in a minute). Any process, such as a comparison, using the rates is to be modified accordingly when the intervals are used instead. For example, if a tachycardia is detected when the ventricular rate exceeds a tachycardia threshold rate, an equivalent process is to detect the tachycardia when the ventricular interval falls below a tachycardia threshold interval. The appended claims should be construed to cover such variations. For example, atrial and ventricular intervals should be construed as equivalent to the atrial and ventricular rates, respectively.

It is to be understood that the above detailed description is intended to be illustrative, and not restrictive. For example, system 100 or system 200 is not limited to applications in an ICD, but may be incorporated into any arrhythmia analysis system, such as a computer program for analyzing pre-collected cardiac data. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system for discriminating ventricular tachycardia (VT) from supraventricular tachycardia (SVT), the system comprising:
    a sensing circuit that senses an atrial electrogram indicative of atrial depolarizations and a ventricular electrogram indicative of ventricular depolarizations;
    a rate detector circuit, coupled to the sensing circuit, that detects an atrial rate based on the atrial electrogram and a ventricular rate based on the ventricular electrogram;
    a tachycardia detector circuit, coupled to the rate detector circuit, that detects a tachycardia based on at least one of the atrial rate and the ventricular rate;
    a rhythm classifier circuit, coupled to the rate detector circuit and the tachycardia detector circuit, that classi-
fies the detected tachycardia as a 1:1 tachycardia in response to the atrial rate and the ventricular rate being substantially equal; and
    a tachycardia discriminator circuit coupled to the rhythm classifier circuit, the tachycardia discriminator circuit including:
        a time interval measurement circuit, coupled to the sensing circuit, that measures a tachycardia time interval between an atrial depolarization and an adjacent ventricular depolarization during the 1:1 tachycardia; and
        a VT comparator circuit coupled to the time interval measurement circuit, the VT comparator circuit having an output that indicates a VT detection in response to the VT comparator circuit determining that the tachycardia time interval differs from a template time interval by at least a predetermined percentage of the template time interval and that indicates a detection of SVT in response to the VT comparator circuit determining that the tachycardia time interval does not differ from the template time interval by at least the predetermined percentage of the template time interval,
    wherein the template time interval is a time interval between an atrial depolarization and an adjacent ventricular depolarization measured during a normal sinus rhythm.

2. The system of claim 1, wherein the time interval measurement circuit comprises an atrioventricular interval (AVI) measurement module that measures a tachycardia AVI in response to the detection of the tachycardia and the classification of the 1:1 tachycardia.

3. The system of claim 2, wherein the AVI measurement module measures the template time interval as an AVI during a normal sinus rhythm.

4. The system of claim 1, wherein the time interval measurement circuit comprises a ventriculoatrial interval (VAI) measurement module that measures a tachycardia VAI in response to the detection of the tachycardia and the classification of the 1:1 tachycardia.

5. The system of claim 4, wherein the VAI measurement module measures the template time interval as a VAI during a normal sinus rhythm.

6. The system of claim 1, wherein the output of the VT comparator circuit indicates an SVT detection in response to the tachycardia time interval not differing from the template time interval by at least the predetermined percentage of the template time interval.

7. The system of claim 1, wherein the tachycardia detector circuit comprises a tachycardia comparator circuit having a tachycardia output indicative a detected tachycardia in response to the ventricular rate exceeding a predetermined tachycardia threshold rate.

8. The system of claim 7, wherein the rhythm classifier circuit comprises a rhythm comparator circuit that compares the atrial rate to the ventricular rate after the tachycardia is detected, the rhythm comparator circuit having an atrial rate input to receive the atrial rate, a ventricular rate input to receive a ventricular rate, and a classification output indicative of VT if the ventricular rate is substantially higher than the atrial rate, SVT or dual arrhythmia if the atrial rate is substantially higher than the ventricular rate, and the 1:1 tachycardia if the atrial rate and the ventricular rate are substantially equal, wherein the dual arrhythmia includes a combination of SVT and VT.

9. The system of claim 8, further comprising an atrial fibrillation (AF) detector circuit, coupled to the rhythm classifier, to detect AF.

10. The system of claim 9, further comprising an atrial defibrillation circuit, coupled to the AF detector circuit, that delivers one or more atrial defibrillation shocks in response to the detection of AF.

11. The system of claim 8, further comprising a ventricular fibrillation (VF) detector circuit, coupled to the rhythm classifier circuit, to detect VF.

12. The system of claim 11, further comprising a ventricular defibrillation circuit, coupled to the VF detector circuit, that delivers one or more ventricular defibrillation shocks in response to the detection of VF.

13. The system of claim 1, wherein the tachycardia discriminator circuit further comprises a VT verifier circuit, coupled to the VT comparator circuit that verifies the VT detection.

14. The system of claim 13, wherein the VT verifier circuit comprises a further tachycardia discriminator circuit.

15. The system of claim 1, comprising an implantable cardiovertor/defibrillator including a hermetically sealed implantable can to house a cardiovertor/defibrillator circuit including at least the sensing circuit, the rate detector circuit, the tachycardia detector circuit, the rhythm classifier circuit, and the tachycardia discriminator circuit.

16. A cardiac rhythm management (CRM) system, comprising:
an implantable atrial lead allowing for sensing an atrial electrogram indicative of atrial depolarizations;
an implantable ventricular lead allowing for sensing a ventricular electrogram indicative of ventricular depolarizations; and
an implantable cardioverter/defibrillator (ICD) including:
a sensing circuit, coupled to the implantable atrial lead and the implantable ventricular lead, to sense the atrial electrogram and the ventricular electrogram;
a rate detector circuit, coupled to the sensing circuit, that detects an atrial rate based on the atrial electrogram and a ventricular rate based on the ventricular electrogram;
a tachycardia detector circuit, coupled to the rate detector circuit, that detects a tachycardia based on at least one of the atrial rate and the ventricular rate;
a rhythm classifier circuit, coupled to the rate detector circuit and the tachycardia detector circuit, that classifies the detected tachycardia as a 1:1 tachycardia in response to the atrial rate and the ventricular rate being substantially equal; and
a tachycardia discriminator circuit coupled to the rhythm classifier circuit, the tachycardia discriminator circuit including:
a time interval measurement circuit, coupled to the sensing circuit, that measures a tachycardia time interval between an atrial depolarization and an adjacent ventricular depolarization during the 1:1 tachycardia; and
a VT comparator circuit coupled to the time interval measurement circuit, the VT comparator circuit having an output that indicates a detection of VT in response to the VT comparator circuit determining that the tachycardia time interval differs from a template time interval by at least a predetermined percentage of the template time interval and that indicates an SVT detection in response to the VT comparator circuit determining that the tachycardia time interval does not differ from the template time interval by at least the predetermined percentage of the template time interval,
wherein the template time interval is a time interval between an atrial depolarization and an adjacent ventricular depolarization measured during a normal sinus rhythm.

17. The CRM system of claim 16, wherein the time interval measurement circuit comprises an atrioventricular interval (AVI) measurement module that measures a tachycardia AVI in response to the detection of the tachycardia and the classification of the 1:1 tachycardia.

18. The CRM system of claim 16, wherein the time interval measurement circuit comprises a ventriculoatrial interval (VAI) measurement module that measures a tachycardia VAI in response to the detection of the tachycardia and the classification of the 1:1 tachycardia.

19. The CRM system of claim 16, wherein the tachycardia detector circuit comprises a tachycardia comparator circuit having a tachycardia output indicative a detected tachycardia in response to the ventricular rate exceeding a predetermined tachycardia threshold rate.

20. The CRM system of claim 19, wherein the rhythm classifier circuit comprises a rhythm comparator circuit that compares the atrial rate to the ventricular rate after the tachycardia is detected, the rhythm comparator circuit having an atrial rate input to receive the atrial rate, a ventricular rate input to receive a ventricular rate, and a classification output indicative of VT if the ventricular rate is substantially higher than the atrial rate, SVT or dual arrhythmia if the atrial rate is substantially higher than the ventricular rate, and the 1:1 tachycardia if the atrial rate and the ventricular rate are substantially equal, wherein the dual arrhythmia includes a combination of SVT and VT.

21. The CRM system of claim 16, wherein the LCD further comprises an atrial fibrillation (AF) detector circuit, coupled to the rhythm classifier circuit, that detects AF if SVT is indicated.

22. The CRM system of claim 21, wherein the LCD further comprises an atrial defibrillation circuit, coupled to the AF detector circuit, that delivers one or more atrial defibrillation shocks in response to the detection of AF.

23. The CRM system of claim 16, wherein the LCD further comprises a ventricular fibrillation (VF) detector circuit, coupled to the rhythm classifier circuit and the VT discriminator circuit, that detects VF if VT is detected.

24. The CRM system of claim 23, wherein the ICD further comprises a ventricular defibrillation circuit, coupled to the VF detector circuit, that delivers one or more ventricular defibrillation shocks in response to the detection of VF.

25. The CRM system of claim 16, wherein the ICD further comprises a VT verifier circuit, coupled to the VT discriminator circuit, that verifies VT detections.

26. The CRM system of claim 25, wherein the VT verifier comprises a further tachycardia discriminator circuit.

27. The CRM system of claim 16, further comprising an external system including an external device communicatively coupled to the LCD via telemetry, a remote device providing for access to the LCD from a distant location, and a network communicatively coupling the external device and the remote device.

28. A method for discriminating ventricular tachycardia (VT) from supraventricular tachycardia (SVT), the method comprising:
detecting a ventricular rate being a frequency of ventricular depolarizations;
detecting an atrial rate being a frequency of atrial depolarizations;
detecting a tachycardia based on at least one of the atrial and ventricular rates;

classifying the tachycardia as a 1:1 tachycardia if the detected atrial rate is substantially the same as the detected ventricular rate;

measuring a tachycardia time interval between adjacent atrial and ventricular depolarizations during the 1:1 tachycardia;

determining whether the tachycardia time interval differs from a template time interval by at least a predetermined percentage of the template time interval;

indicating a VT detection if the determining indicates that the tachycardia time interval differs from the template time interval by at least the predetermined percentage of the template time interval; and indicating a SVT detection if the determining indicates that the tachycardia time interval does not differ from the template time interval by the predetermined percentage of the template time interval, wherein the template time interval is a time interval between adjacent atrial and ventricular depolarizations measured during a normal sinus rhythm.

29. The method of claim 28, wherein measuring the tachycardia time interval comprises measuring a tachycardia atrioventricular interval (AVI) during the 1:1 tachycardia, and wherein indicating the VT detection comprises indicating the VT detection if the tachycardia AVI exceeds a template AVI by at least a predetermined percentage of the template AVI.

30. The method of claim 29, further comprising creating the template AVI by measuring an AVI during a normal sinus rhythm.

31. The method of claim 28, wherein measuring the tachycardia time interval comprises measuring a tachycardia ventriculoatrial interval (VAI) and a tachycardia heart rate during the 1:1 tachycardia, and wherein indicating the VT detection comprises adjusting the tachycardia VAI based on the tachycardia heart rate and a template heart rate, and indicating the VT detection if a template VAI exceeds the adjusted tachycardia VAL by a predetermined percentage of the template VAI.

32. The method of claim 31, further comprising:
creating the template VAI by measuring a VAI during a normal sinus rhythm; and
creating the template heart rate by measuring a heart rate during the normal sinus rhythm.

33. The method of claim 28, further comprising performing a statistical study based on a patient population to determine the predetermined percentage of the template time interval.

34. The method of claim 28, wherein detecting the ventricular rate comprises sensing a ventricular electrogram indicative of ventricular depolarizations, and detecting the atrial rate comprises sensing an atrial electrogram indicative of atrial depolarizations.

35. The method of claim 34, wherein detecting tachycardia comprises comparing the detected ventricular rate to a predetermined tachycardia threshold rate.

36. The method of claim 35, further comprising classifying the tachycardia as VT if the detected ventricular rate is substantially higher than the detected atrial rate.

37. The method of claim 36, further comprising detecting ventricular fibrillation (VF).

38. The method of claim 35, further comprising delivering at least one ventricular defibrillation shock if VF is detected.

39. The method of claim 35, further comprising classifying the tachycardia as SVT or dual arrhythmia if the detected atrial rate is substantially higher than the detected ventricular rate, wherein the dual arrhythmia includes a combination of SVT and VT.

40. The method of claim 39, further comprising detecting atrial fibrillation (AF).

41. The method of claim 40, further comprising delivering at least one atrial defibrillation shock if AF is detected.

42. The method of claim 28, further comprising confirming the VT detection after indicating the VT detection.

* * * * *

UNITED STATES PATENT AND TRADEMARK OFFICE
CERTIFICATE OF CORRECTION

PATENT NO. : 7,515,956 B2  Page 1 of 1
APPLICATION NO. : 10/844475
DATED : April 7, 2009
INVENTOR(S) : Julie A. Thompson It is certified that error appears in the above-identified patent and that said Letters Patent is hereby corrected as shown below:

In column 1, line 9, delete "6,959,212" and insert -- 6,959,212, --, therefor.

In column 1, line 11, delete "6,889,081" and insert -- 6,889,081, --, therefor.

In column 1, lines 17-18, delete "7,062,316" and insert -- 7,062,316, --, therefor.

In column 12, line 31, in Claim 2, delete "1:1tachycardia." and insert -- 1:1 tachycardia. --, therefor.

In column 12, line 39, in Claim 4, delete "1:1tachycardia." and insert -- 1:1 tachycardia. --, therefor.

In column 14, lines 28-29, in Claim 20, delete "1:1tachycardia" and insert -- 1:1 tachycardia --, therefor.

In column 14, line 32, in Claim 21, delete "LCD" and insert -- ICD --, therefor.

In column 14, line 36, in Claim 22, delete "LCD" and insert -- ICD --, therefor.

In column 14, line 40, in Claim 23, delete "LCD" and insert -- ICD --, therefor.

In column 14, line 55, in Claim 27, delete "LCD" and insert -- ICD --, therefor.

In column 14, line 56, in Claim 27, delete "LCD" and insert -- ICD --, therefor.

In column 15, line 37, in Claim 31, delete "VAL" and insert -- VAI --, therefor.

Signed and Sealed this

Fifth Day of January, 2010

David J. Kappos
*Director of the United States Patent and Trademark Office*